United States Patent
Bhalerao et al.

(10) Patent No.: US 10,544,101 B2
(45) Date of Patent: Jan. 28, 2020

(54) PROCESS FOR THE PREPARATION OF BUTORPHANOL TARTRATE

(71) Applicant: Hikal Limited, Pune (IN)

(72) Inventors: Rahul Bhalerao, Pune (IN); R. Sridharan, Pune (IN); Shivaji Sadashiv Kandre, Pune (IN); Ganesh Suryakant Deore, Pune (IN); Kishorkumar Shivajirao Kadam, Pune (IN); Dharnidhar Mundhe, Pune (IN)

(73) Assignee: Hikal Limited, Pune (IN)

( * ) Notice: Subject to any disclaimer, the term of this patent is extended or adjusted under 35 U.S.C. 154(b) by 0 days.

(21) Appl. No.: 16/089,505

(22) PCT Filed: Mar. 27, 2017

(86) PCT No.: PCT/IN2017/050112
§ 371 (c)(1),
(2) Date: Sep. 28, 2018

(87) PCT Pub. No.: WO2017/168444
PCT Pub. Date: Oct. 5, 2017

(65) Prior Publication Data
US 2019/0112273 A1   Apr. 18, 2019

(30) Foreign Application Priority Data
Mar. 29, 2016 (IN) .............................. 201621010777

(51) Int. Cl.
*C07D 491/08* (2006.01)
*C07D 221/28* (2006.01)
*C07D 217/26* (2006.01)

(52) U.S. Cl.
CPC ......... *C07D 221/28* (2013.01); *C07D 217/26* (2013.01); *C07D 491/08* (2013.01)

(58) Field of Classification Search
CPC ... C07D 221/28; C07D 491/08; C07D 217/26
USPC ........................................................ 546/115
See application file for complete search history.

(56) References Cited

PUBLICATIONS

Copp et al., "A Novel Ring Closure Leading to 3,9-dihydroxyaporphines (3,9-dihydroxy-4H-dibenzo[de,g]quinolines)," J. Chem. Soc., Perkin Trans. 1, 0:2455-2462, Jan. 1985.
International Search Report and Written Opinion of the ISA/IN dated Jun. 12, 2017 in International Application No. PCT/IN2017/050112; 8pgs.
Monković et al. "A Stereo Selective Total 1-19 Synthesis of 14-Hydroxymorphinans, Grewe Approach," J. Am Chem Soc., 100(14):4609-4610, Jul. 1978.

*Primary Examiner* — Taylor V Oh
(74) *Attorney, Agent, or Firm* — Haukaas Fortius PLLC; Michael Haukaas

(57) ABSTRACT

The present invention relates to an improved process for the preparation of Butorphanol tartrate of formula (I), (I)

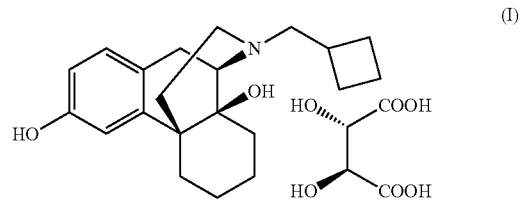

22 Claims, No Drawings

PROCESS FOR THE PREPARATION OF BUTORPHANOL TARTRATE

FIELD OF INVENTION

The present invention is in the field of chemistry, and more particularly the present invention relates to a preparation of Butorphanol tartrate in a very safe, economical, and user-friendly process using novel intermediates.

BACKGROUND OF INVENTION

Butorphanol tartrate (I), is chemically known as N-cyclobutylmethyl-3,14-dihydroxymorphinan tartrate, which is a morphinan-type synthetic opioid analgesic of phenanthrene series and is highly effective for the treatment of both chronic and acute pain. Parenterally administered Butorphanol tartrate is more potent than morphine and most other morphine analogs. Parenteral formulations of Butorphanol tartrate and its use for the relief of acute and chronic pain are first disclosed in the U.S. Pat. No. 3,775,414 (hereinafter referred to as '414) and U.S. Pat. No. 3,819,635 (hereinafter referred to as '635). A parenteral formulation of Butorphanol tartrate is commercially available under the name Stadol® from Bristol-Myers Laboratories, Inc. The chemical structure of Butorphanol tartrate (I) is depicted below:

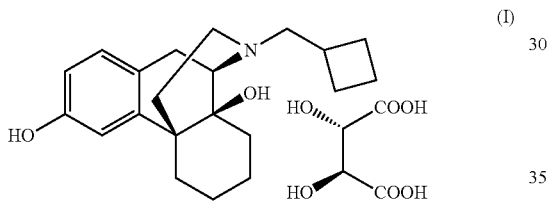

The preparations of 14-hydroxymorphinan derivatives are schematically presented in scheme (1) and are disclosed in the aforesaid U.S. Pat. No. '414. The scheme (1) consists of the condensation of 7-methoxy-3,4-dihydro-1(2H)-naphthalenone with 1,4 dibromobutane by means of sodium hydride (NaH) in benzene gives 3,4-dihydro-7-methoxy-2,2-tetramethylene-1(2H)-naphthalenone, which is treated with acetonitrile and n-butyllithium in tetrahydrofuran (THF) yielding 1-hydroxy-7-methoxy-1,2,3,4-tetrahydro-2,2-tetramethylene-1-naphthaleneacetonitrile. This compound is reduced with lithium aluminium hydride (LAH or LiAlH$_4$) in THF to afford hydro-2,2-tetramethylene-1-naphthol and isomerized to 4a-(2-aminoethyl)-1,2,3,4,4a,9-hexahydro-6-methoxy-phenantrene. This amine is cyclized by reaction with bromine in chloroform (CHCl$_3$) giving 3-methoxy-9a-bromonrhasybanan hydrobromide and isomerized with dehydrobromination by treatment with sodium bicarbonate (NaHCO$_3$) in N,N-Dimethylformamide (DMF) affording 3-methoxy-DELTA(8,14)-morphinan. Further acetylation with trifluoroacetic anhydride yields 3-methoxy-N-trifluoroacetyl-DELTA(8,14)-morphinan, which is epoxidized with m-chloroperbenzoic acid (m-CPBA) in dichloromethane (DCM) giving 8,14-epoxy-3-methoxy-N-trifluoroacetylmorphina, which is further treated with sodium borohydride (NaBH$_4$) in ethanol gives 8,14-epoxy-3-methoxymorphinan as an oily product that is treated with LiAlH$_4$ in THF to open the epoxide ring and yield 14-hydroxy-3-methoxymorphinan. The condensation of 14-hydroxy-3-methoxymorphinan with cyclobutylcarbonyl chloride by means of pyridine in DCM affords N-cyclobutylcarbonyl-14-hydroxy-3-methoxymorphinan, which is reduced with LiAlH$_4$ in refluxing THF giving N-cyclobutylmethyl-14-hydroxy-3-methoxymorphinan. Finally, it is demethylated by treatment with refluxing 48% hydrogen bromide (HBr) to provide N-cyclobutylmethyl-3,14-dihydroxymorphinan.

Scheme-1

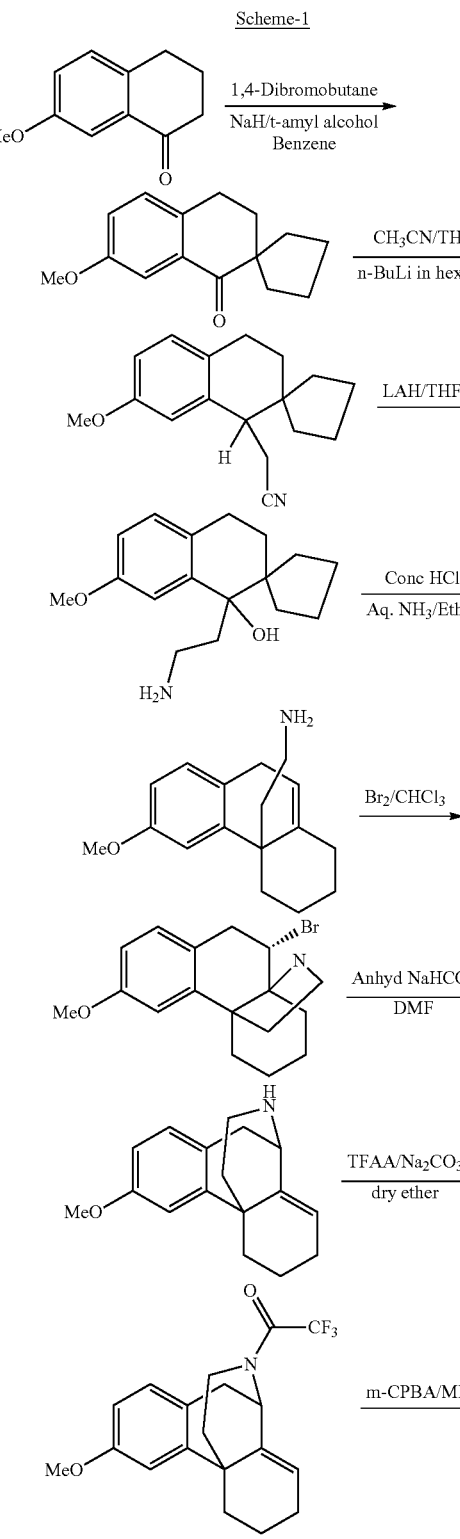

-continued

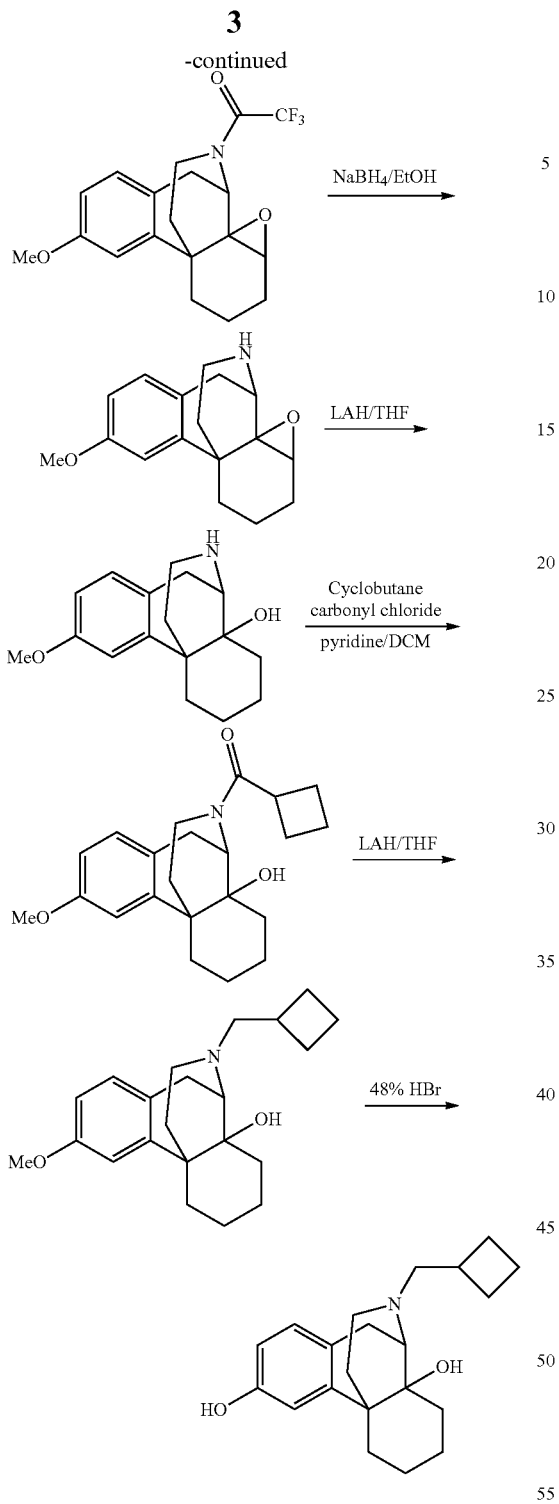

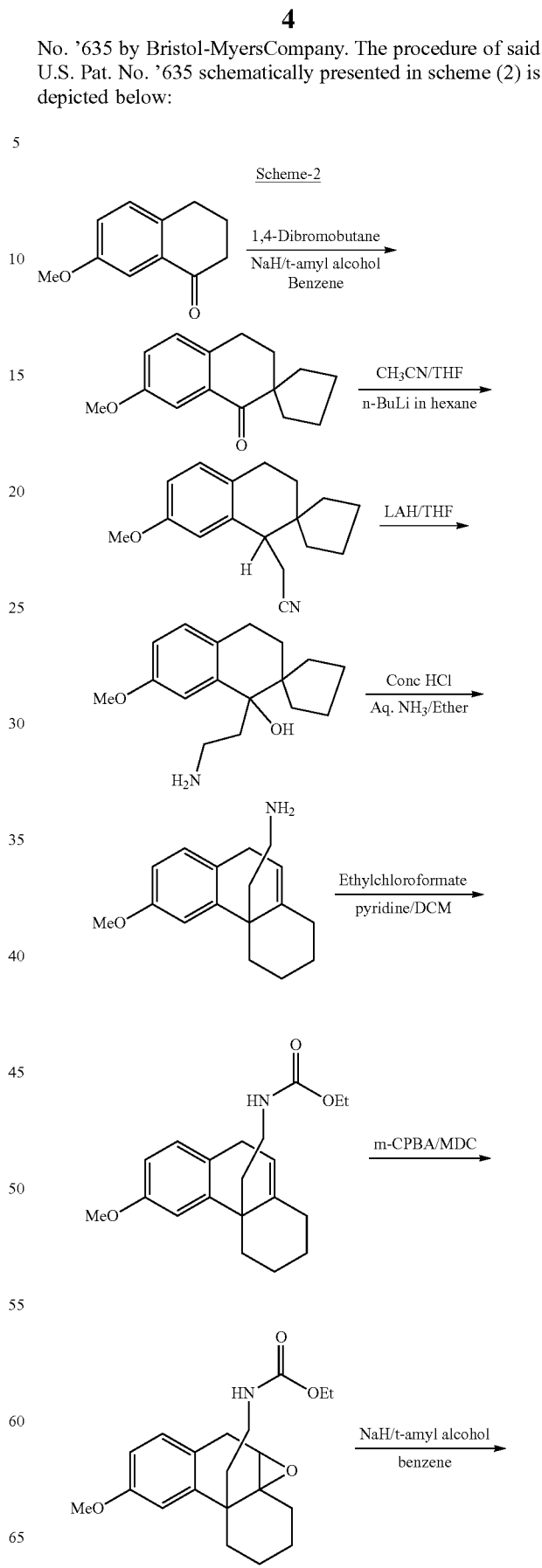

No. '635 by Bristol-MyersCompany. The procedure of said U.S. Pat. No. '635 schematically presented in scheme (2) is depicted below:

The process disclosed in U.S. Pat. No. '414 involves the use of 7-methoxy-3,4-dihydro-1(2H)-naphthalenone compound as the starting material which undergoes a series of reaction steps to finally form Butorphanol, whereas the starting material used in the process involved in the present invention the reaction of 4-methoxyphenylacetic acid with 2-(1-cyclohexenyl)ethylamine compound leads to formation of Butorphanol and its salt via novel intermediates. Moreover, the process in the U.S. Pat. No. '414 does not discloses anywhere the formation of tartrate salt of Butorphanol.

The Butorphanol may also be prepared by another alternative synthetic procedure described in the said U.S. Pat.

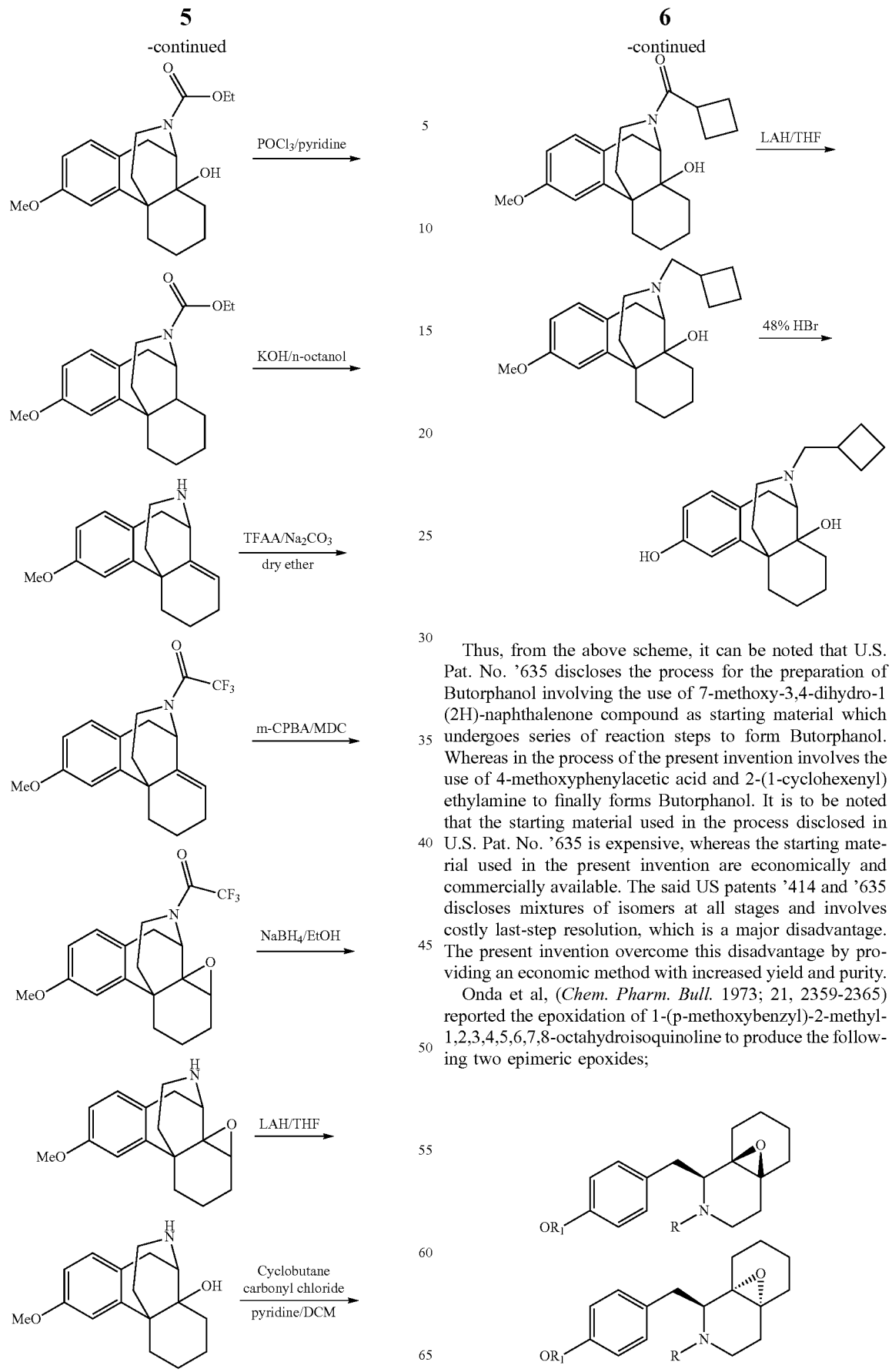

Thus, from the above scheme, it can be noted that U.S. Pat. No. '635 discloses the process for the preparation of Butorphanol involving the use of 7-methoxy-3,4-dihydro-1 (2H)-naphthalenone compound as starting material which undergoes series of reaction steps to form Butorphanol. Whereas in the process of the present invention involves the use of 4-methoxyphenylacetic acid and 2-(1-cyclohexenyl) ethylamine to finally forms Butorphanol. It is to be noted that the starting material used in the process disclosed in U.S. Pat. No. '635 is expensive, whereas the starting material used in the present invention are economically and commercially available. The said US patents '414 and '635 discloses mixtures of isomers at all stages and involves costly last-step resolution, which is a major disadvantage. The present invention overcome this disadvantage by providing an economic method with increased yield and purity.

Onda et al, (*Chem. Pharm. Bull.* 1973; 21, 2359-2365) reported the epoxidation of 1-(p-methoxybenzyl)-2-methyl-1,2,3,4,5,6,7,8-octahydroisoquinoline to produce the following two epimeric epoxides;

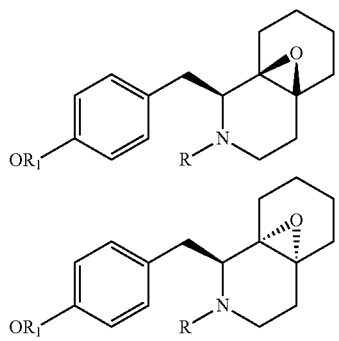

and the diols resulting there from having the following intermediates,

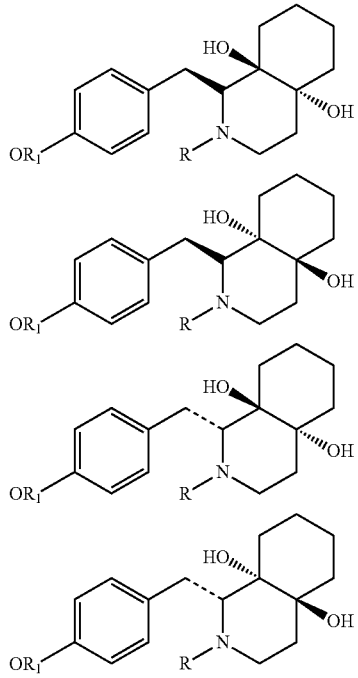

Nothing in this paper describes, anticipates or teaches the preparation of the 9,10-diols in which the N-methyl is alkanoyl. The prior art has certain disadvantage and the present invention provides a novel process to synthesize 14-hydroxymorphinans via novel epoxide intermediate with surprisingly better results which overcome the disadvantage of the prior art.

Schnider and Hellerback (*Helv. Chim. Acta.,* 1951; 34, 2218-2222) describes the preparation of morphinan from the same starting materials as used in the instant invention.

Schnider, Brossi and Vogler (*Helv. Chim. Acta.,* 1954; 37, 710-720) further describes the preparation of 14-deoxymorphinans from the same starting materials as used in the instant invention.

Schnider and Hellerback (*Helv. Chim. Acta.,* 1950; 33, 1437-1448) describes the preparation of 14-deoxymorphinans from the same starting materials as used in the instant invention. These prior arts do not link or suggest that 14-hydroxymorphinans could be prepared via this route.

U.S. Pat. No. 3,919,237 discloses the cyclization of following compounds and the derivatives thereof into is morphinans and morphinan using boron trifluoride and a proton/hydronium ion donor as the cyclization catalyst. None of the compounds so produced have a 14-hydroxy substituent.

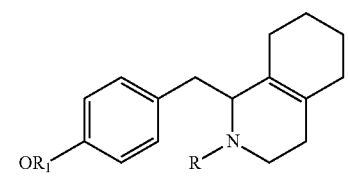

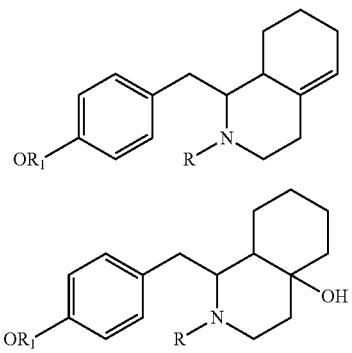

U.S. Pat. No. 4,052,389 discloses the protection of racemic 1-(4-methoxy-benzyl)-1,2,3,4,5,6,7,8-octahydro-isoquinoline using trifluoroacetic anhydride or ethyl formate or methyl chloroformate, whereas in present invention 1-(4-methoxy-benzyl)-1,2,3,4,5,6,7,8-octahydro-isoquinoline was resolved with mandelic acid and further protected with di-tert-butyl dicarbonate (BOC anhydride) which is different from process involved in the said US '389 patent. The procedure of this patent is schematically presented in scheme (3) is depicted below:

Scheme-3

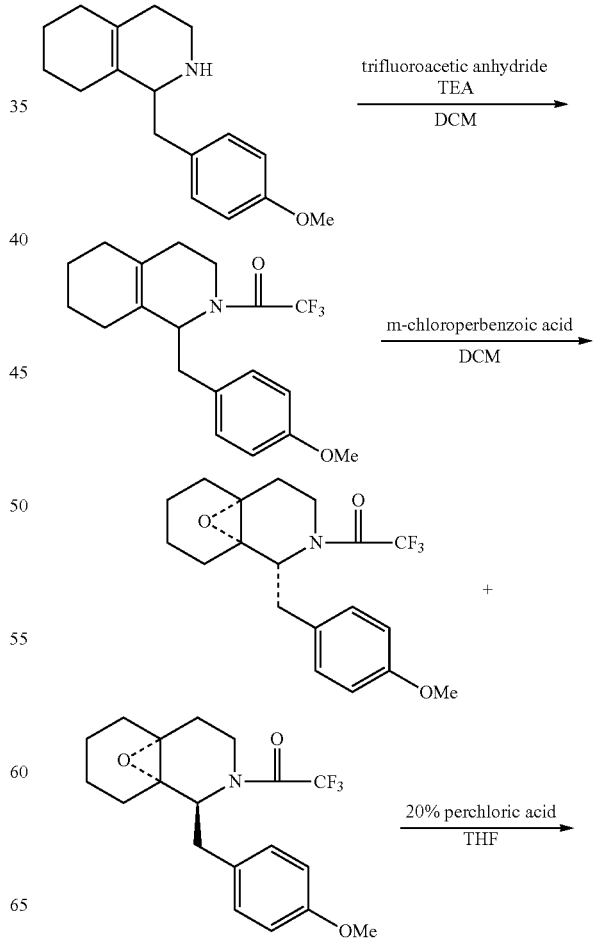

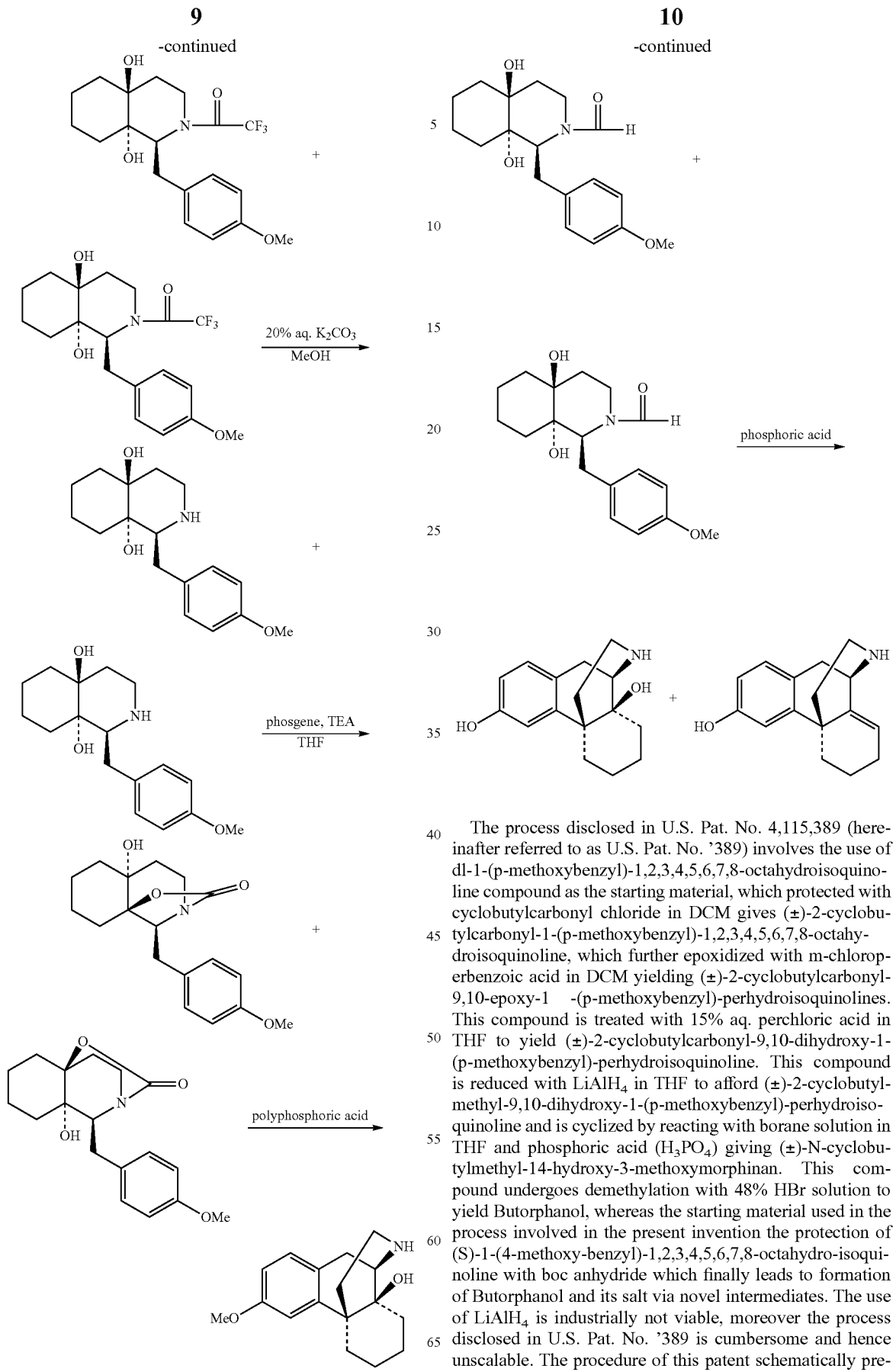

The process disclosed in U.S. Pat. No. 4,115,389 (hereinafter referred to as U.S. Pat. No. '389) involves the use of dl-1-(p-methoxybenzyl)-1,2,3,4,5,6,7,8-octahydroisoquinoline compound as the starting material, which protected with cyclobutylcarbonyl chloride in DCM gives (±)-2-cyclobutylcarbonyl-1-(p-methoxybenzyl)-1,2,3,4,5,6,7,8-octahydroisoquinoline, which further epoxidized with m-chloroperbenzoic acid in DCM yielding (±)-2-cyclobutylcarbonyl-9,10-epoxy-1 -(p-methoxybenzyl)-perhydroisoquinolines. This compound is treated with 15% aq. perchloric acid in THF to yield (±)-2-cyclobutylcarbonyl-9,10-dihydroxy-1-(p-methoxybenzyl)-perhydroisoquinoline. This compound is reduced with LiAlH$_4$ in THF to afford (±)-2-cyclobutylmethyl-9,10-dihydroxy-1-(p-methoxybenzyl)-perhydroisoquinoline and is cyclized by reacting with borane solution in THF and phosphoric acid (H$_3$PO$_4$) giving (±)-N-cyclobutylmethyl-14-hydroxy-3-methoxymorphinan. This compound undergoes demethylation with 48% HBr solution to yield Butorphanol, whereas the starting material used in the process involved in the present invention the protection of (S)-1-(4-methoxy-benzyl)-1,2,3,4,5,6,7,8-octahydro-isoquinoline with boc anhydride which finally leads to formation of Butorphanol and its salt via novel intermediates. The use of LiAlH$_4$ is industrially not viable, moreover the process disclosed in U.S. Pat. No. '389 is cumbersome and hence unscalable. The procedure of this patent schematically presented in scheme (4) is depicted below:

Scheme-4
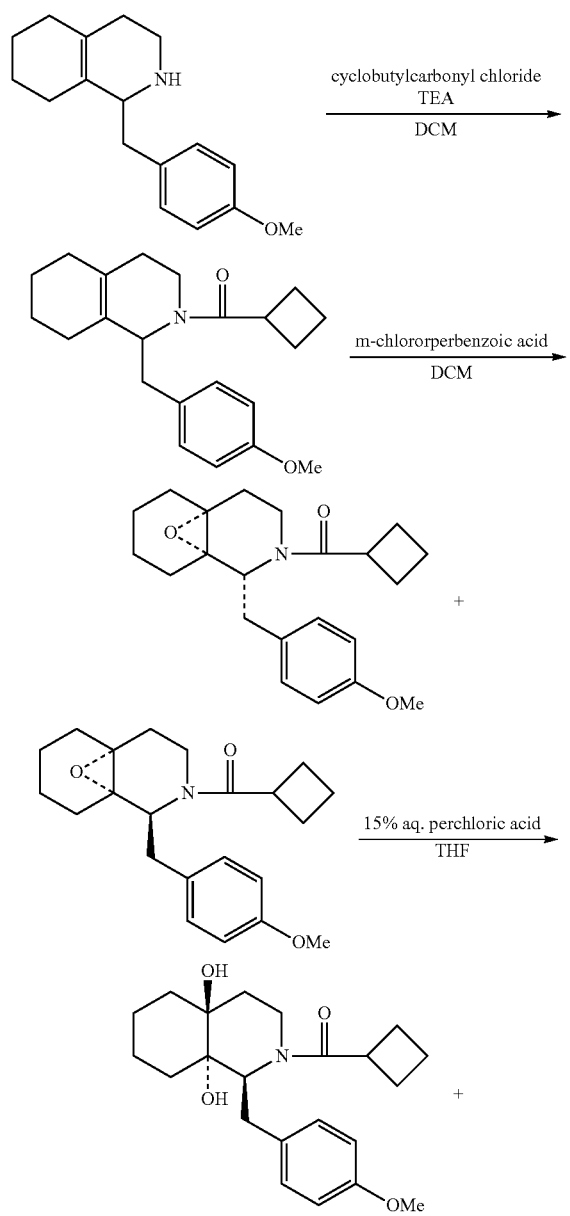
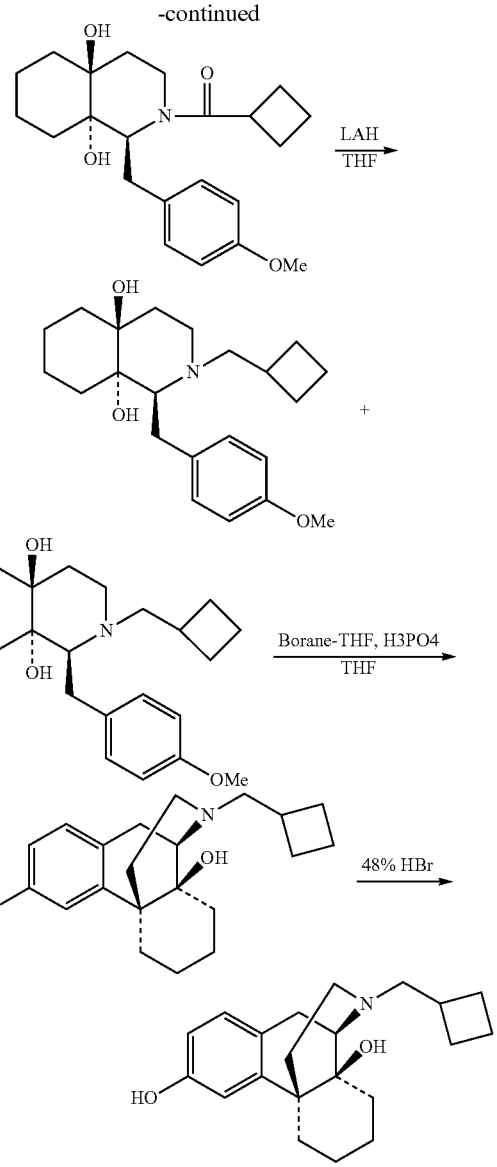
The procedure of U.S. Pat. No. 2,634,292 (hereinafter referred to as U.S. Pat. No. '292) and U.S. Pat. No. 2,634,273 (hereinafter referred to as U.S. Pat. No. '273) are schematically presented in scheme (5) is depicted below:
Scheme-5
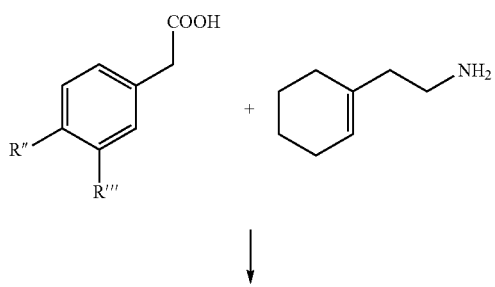

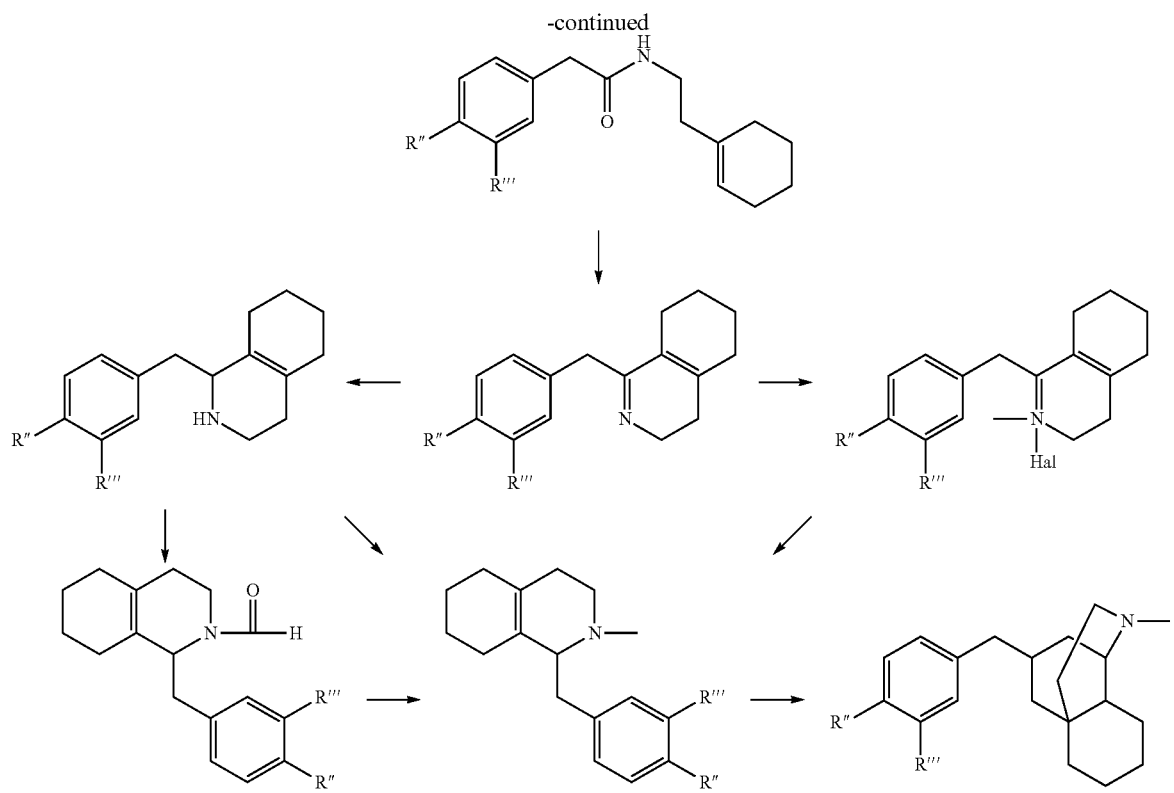

From the scheme (5) it can be noted that the process disclosed by U.S. Pat. No. '273 involves the reaction of cyclohexene-(1)-yl-ethylamine with phenylacetic acid to form corresponding phenyl acetic acid (cyclohexenyl-ethyl) amide. However, this process proceeds through different intermediates and this patent does not suggest the use of this process for butorphanol. The present invention differs from the process set out in scheme 5 by the use of novel intermediate and use of the said process to obtain butorphanol. Hence, there is no suitable process in the prior art for synthesis of butorphenol with high yield and purity and in economic manner. Therefore, there is a need for an economic process for the synthesis of butorphenol in high yield and purity.

OBJECTS OF THE INVENTION

An object of the present invention is to provide an improved process for the preparation of a compound of formula (I), which is simple, economical, user- friendly and commercially viable.

Another object of the present invention is to provide a process for the preparation of a compound of formula (I), which would be easy to implement on commercial scale, and to avoids the use of expensive reagent(s) and hazardous organic solvent(s), which makes the present invention eco-friendly as well.

Yet another object of the present invention is to provide a process for the preparation of a compound of formula (I) in a greater yield with higher chemical & chiral purity.

Yet another object of the present invention is to provide a process for the preparation of a compound of formula (IVc), wherein the byproduct formed of formula (IVd) during the reaction can be reusable and thereby recyclable, which makes the process industrially more suitable.

Yet another object of the present invention is to provide novel compound of Formula (V), Formula (VIa) and Formula (VIb) of the N-substituted-isoquinoline derivatives.

Still another object of the present invention is to provide novel process for preparation of Formula (V), Formula (VIa) and Formula (VIb) of the N-substituted-isoquinoline derivatives.

SUMMARY OF THE INVENTION

Accordingly, the present invention provides an improved process for the preparation of Butorphanol tartrate of formula (I).

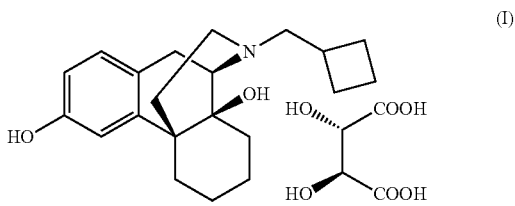

(I)

comprising the steps of;
  (a) obtaining a compound of formula (IV) by reacting a compound of formula (II) with a compound of formula (III) in suitable conditions;
  (b) resolving a compound of formula (IV) to obtain a mixture of compound of formula (IVa) and (IVb) using a suitable resolving agent in a suitable solvent to further obtain a mixture of compound of formula (IVc) and (IVd);
  (c) protecting a compound of formula (IVc) with di-tert-butyl dicarbonate in presence of a suitable base in a suitable solvent to get a compound of formula (V);

(d) obtaining a mixture of compound of formula (VIa) and (VIb) by the epoxidation of compound of formula (V) with peroxy acid in a suitable solvent;

(e) obtaining a mixture of compound of formula (VIIa) and (VIIb) by acid catalyzed ring opening and deprotection of mixture of compounds of formula (VIa) and (VIb) with a suitable acid in a suitable organic solvent;

(f) obtaining a mixture of compound of formula (VIIIa) and (VIIIb) by reacting a mixture of compound of formula (VIIa) and (VIIb) with cyclobutylmethyl bromide in presence of a suitable base in a suitable solvent;

(g) cyclizing a mixture of compound of formula (VIIIa) and (VIIIb) with borane in presence of an anhydrous acid with or without suitable organic solvent to obtain a compound of formula (IX);

(h) demethylating a compound of formula (IX) using a suitable demethylating agent in a suitable solvent to obtain Butorphanol of formula (X); and (i) obtaining Butorphanol tartrate salt of formula (I) from Butorphanol of formula (X) by using tartaric acid in a suitable organic solvent.

The above process is illustrated in the following general synthetic scheme-I:

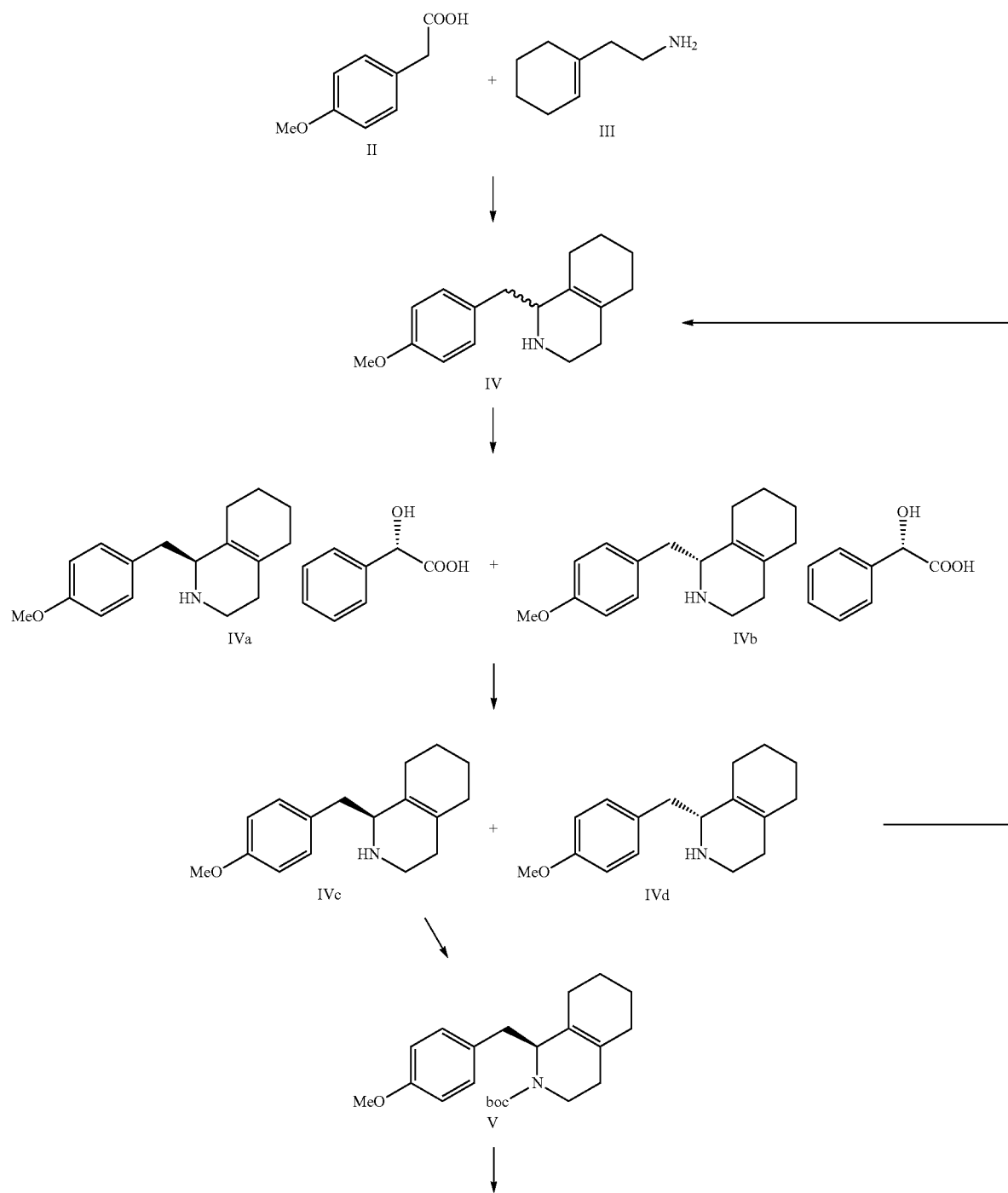

-continued
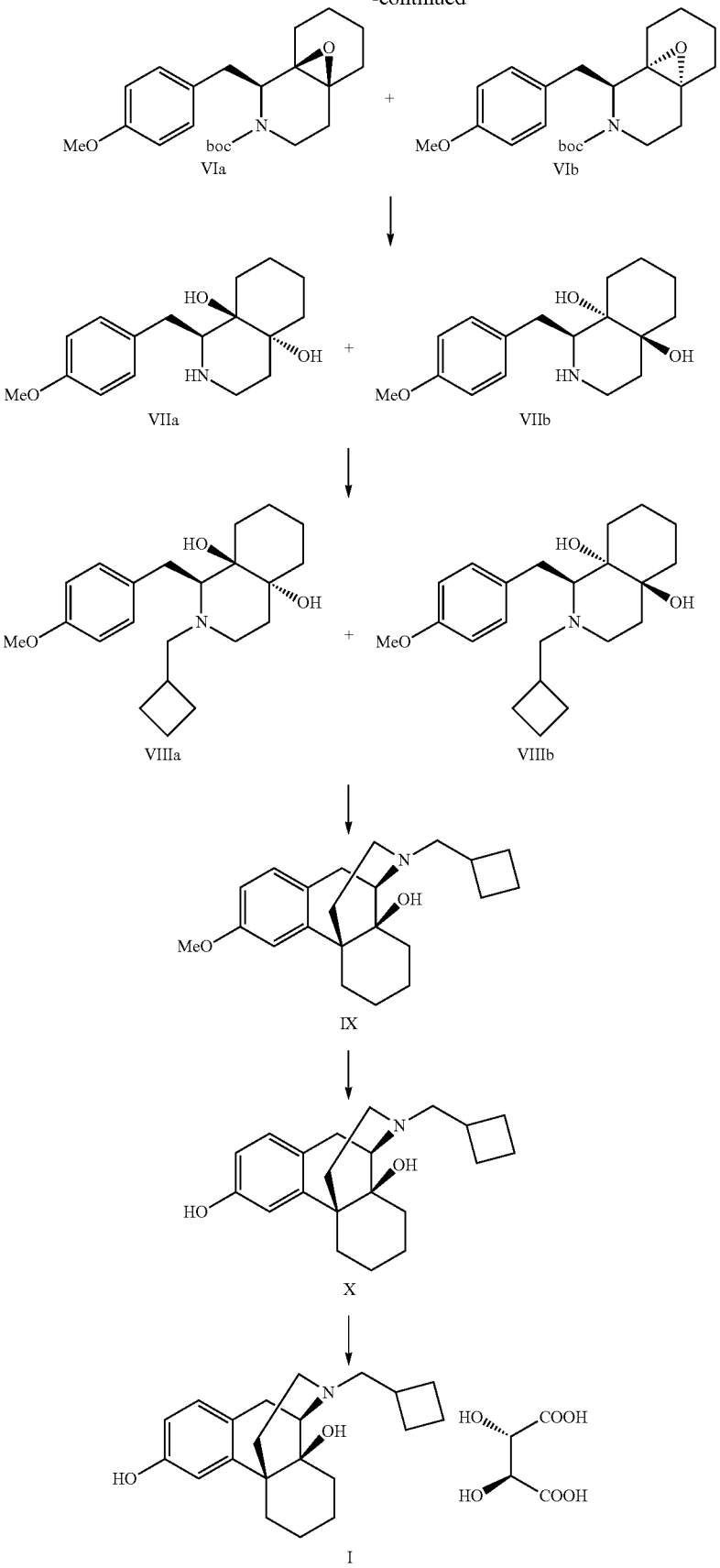

DETAILED DESCRIPTION OF THE INVENTION

The present invention is described more fully hereinafter. The invention may be embodied in many different forms and should not be construed as limited to the embodiments set forth herein; rather, these embodiments are provided so that this disclosure will satisfy applicable legal requirements. As used in the specification and in the appended claims, the singular forms "a", "an", "the", include plural referents unless the context clearly indicates otherwise.

The present invention provides an improved process for the preparation of Butorphanol tartrate of formula (I) via novel synthetic approach using novel intermediates.

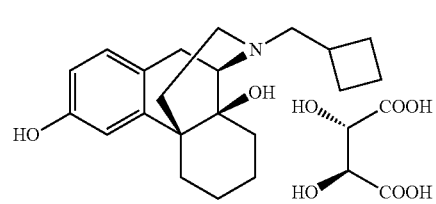
(I)

which comprises the steps of:
(a) obtaining a compound of formula (IV) by reacting a compound of formula (II) with a compound of formula (III) in suitable conditions;

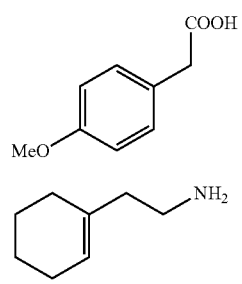
(II)

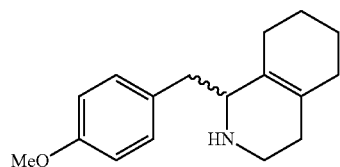
(III)

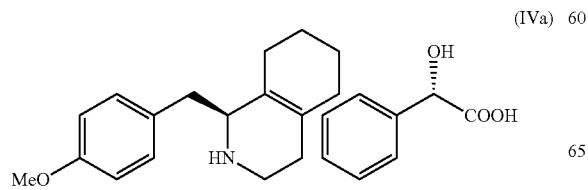
(IV)

(b) resolving a compound of formula (IV) to obtain a mixture of compound of formula (IVa) and (IVb) using a suitable resolving agent in a suitable solvent to further obtain a mixture of compound of formula (IVc) and (IVd);

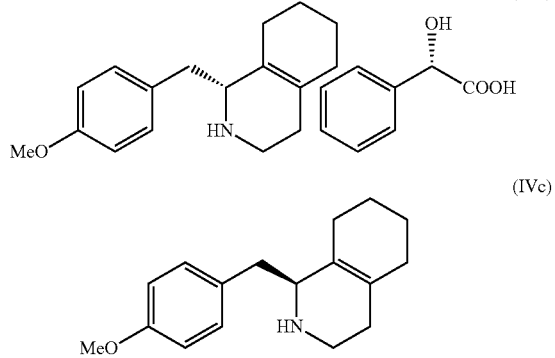
(IVa)
(IVb)
(IVc)
(IVd)

(c) protecting a compound of formula (IVc) with di-tert-butyl dicarbonate in presence of a suitable base in a suitable solvent to get a compound of formula (V);

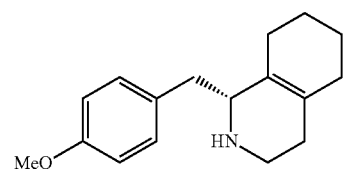
(V)

(d) obtaining a mixture of compound of formula (VIa) and (VIb) by the epoxidation of compound of formula (V) with peroxy acid in a suitable solvent;

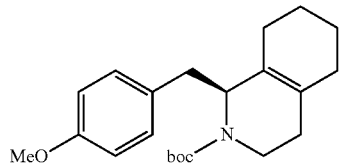
(VIa)

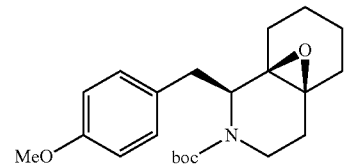
(VIb)

(e) obtaining a mixture of compound of formula (VIIa) and (VIIb) by acid catalyzed ring opening and deprotection of mixture of compounds of formula (VIa) and (VIb) with a suitable acid in a suitable organic solvent;

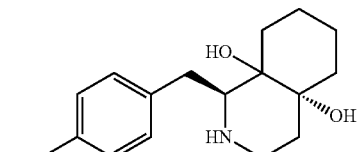
(VIIa)

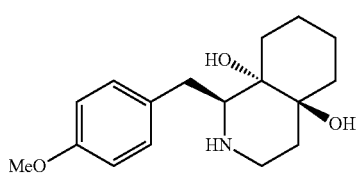
(VIIb)

(f) obtaining a mixture of compound of formula (VIIIa) and (VIIIb) by reacting a mixture of compound of formula (VIIa) and (VIIb) with cyclobutylmethyl bromide in presence of a suitable base in a suitable solvent;

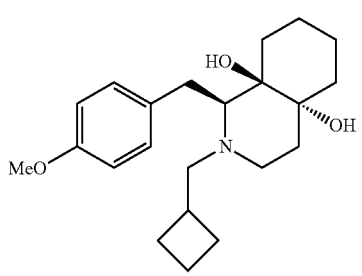
(VIIIa)

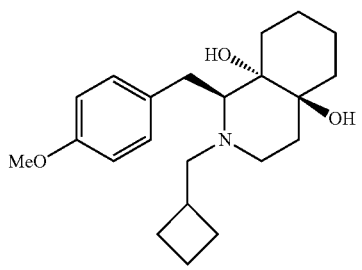
(VIIIb)

(g) cyclizing a mixture of compound of formula (VIIIa) and (VIIIb) with borane in presence of an anhydrous acid with or without suitable organic solvent to obtain a compound of formula (IX);

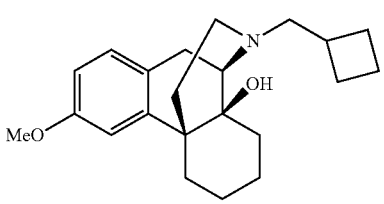
(IX)

(h) demethylating a compound of formula (IX) using a suitable demethylating agent in a suitable solvent to obtain Butorphanol of formula (X); and

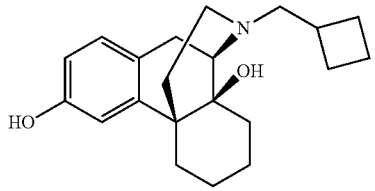
(X)

(i) obtaining Butorphanol tartrate salt of formula (I) from Butorphanol of formula (X) by using tartaric acid in a suitable organic solvent.

The list of starting materials and key intermediates used in the present invention are as follows:

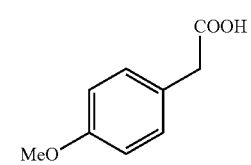
II

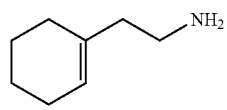
III

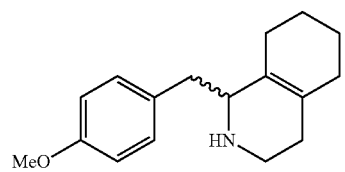
IV

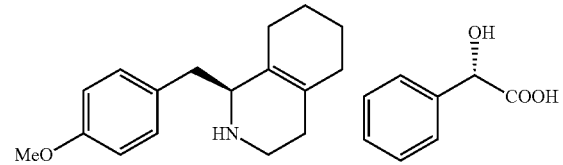
IVa

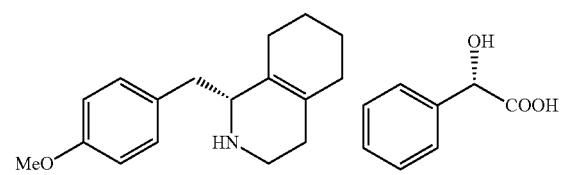
IVb

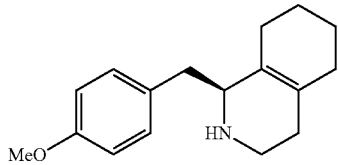
IVc

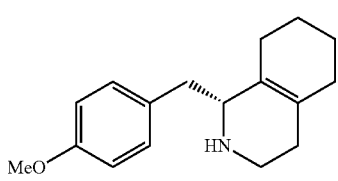
IVd

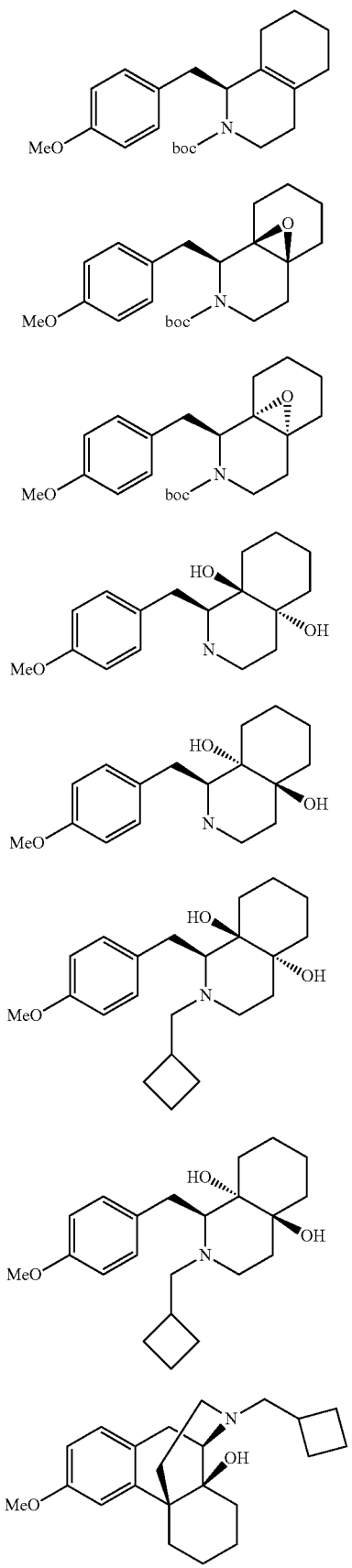

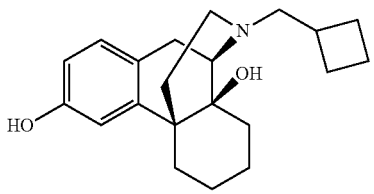

Accordingly, in an embodiment of the present invention, the compound of formula (IV) of step (a) is obtained by following the various steps such as condensation, cyclization and reduction in in-situ manner via suitable conditions described herein. The compound of formula (II) and (III) undergo for the condensation using an organic solvent under reflux conditions. The condensed intermediate is cyclized using an acid and an organic solvent, further cyclized intermediate is undergone for reduction using suitable reducing agent in presence of a suitable base.

In another embodiment of the present invention, wherein the said solvent used in step (a) and step (b) may be preferably selected from the group consisting of water, xylene, benzene, toluene, ethylbenzene, cyclohexane and the like or mixture of solvents thereof; more preferably xylene of step (a) and toluene and water (b).

In another embodiment of the present invention, wherein the said acid used in step (a) is phosphorus oxychloride or any other suitable acid.

In another embodiment of the present invention, wherein the said reducing agent used in step (a) may be preferably selected from the group consisting of sodium borohydride, lithium borohydride, lithium aluminium hydride and the like or mixture thereof; more preferably sodium borohydride.

In another embodiment of the present invention, wherein the said reducing agent used in step (a) may be selected as mixture of sodium borohydride with iodine and the like.

In another embodiment of the present invention, wherein the said base of step (a), step (c) and step (f) may be preferably selected from organic base or an inorganic base. The said organic base is selected from the group consisting of pyridine or mono, di and tri alkyl amine, which are further selected from the group consisting of methyl amine, triethyl amine, diisopropylethyl amine and the like. The said inorganic base is selected from the group consisting of potassium carbonate, sodium carbonate, sodium bicarbonate, potassium bicarbonate, alkali or alkaline earth metal hydroxides such as sodium hydroxide, potassium hydroxide and the like. The preferred base in step (a) is sodium hydroxide, in step (c) is triethyl amine and in step (f) is sodium bicarbonate.

In another embodiment of the present invention, wherein the said resolving agent used in step (b) is S (+) mandelic acid or any suitable resolving agent.

In another embodiment of the present invention, wherein the said solvent used in step (c), step (d), step (e) and step (h) is chlorinated solvent, which may be preferably selected from the group consisting of ethylene dichloride, chloroform, dichloromethane and the like or mixture thereof; more preferably in step (c), step (d), step (e) and step (h) is dichloromethane.

In another embodiment of the present invention, wherein the said peroxy acid used in step (d) is m-chloroperbenzoic acid or any suitable peroxy acid.

In another embodiment of the present invention, wherein the said acid used in step (e) is sulfuric acid ($H_2SO_4$) or any suitable acid.

In another embodiment of the present invention, wherein the said solvent used in step (e) may be preferably selected from the group consisting of water, ketonic solvents such as acetone, methyl ethyl ketone (MEK) and methyl isobutyl ketone (MIBK) and the like or mixture thereof; more preferably is acetone and water.

In another embodiment of the present invention, wherein the said solvent used in step (f) is preferably selected from polar aprotic solvent or mixture thereof; more preferably is N, N-dimethylformamide.

In another embodiment of the present invention, wherein the said acid used in step (g) ispolyphosphoric acid.

In another embodiment of the present invention, wherein the said solvent used in step (g) is tetrahydrofuran or any other suitable solvent, which is in the form of borane-tetrahydrofuran or any other borane-solvent complex.

In another embodiment of the present invention wherein, the said demethylating agent in step (h) may be preferably selected from the group consisting of sodium dithionate, potassium dithionate, barium dithionate, boron tribromide ($BBr_3$), phosphorus tribromide ($PBr_3$) and the like or mixture thereof; more preferably is boron tribromide.

In an embodiment of the present invention wherein, the said solvent used in step (i) may be preferably selected from the group consisting of methanol, ethanol, isopropanol, n-propanol, n-butanol, acetone, methyl ethyl ketone and methyl isobutyl ketone, and the like or mixture thereof; more preferably is methanol and acetone.

In another embodiment of the present invention, wherein all the steps of instant invention may be preferably carried out at 0° C. to ambient temperature or to reflux temperature.

In another embodiment of the present invention, wherein all the steps or some of the steps may be performed in in-situ manner More particularly the step (a) and (b), the step (c), (d) and (e) and step (g) and (h) are performed in-situ manner.

The invention is further illustrated by the following examples, which should not be construed to limit the scope of the invention in anyway.

EXAMPLE 1.0

1-(4-Methoxy-benzyl)-1,2,3,4,5,6,7,8-octahydro-isoquinoline (IV)

To a stirred solution of 4-methoxyphenyl acetic acid of formula (II) (398.2 g, 2.396 moles) in 600 mL of xylene, cyclohexenyl ethylamine of formula (III) (300.0 g, 2.395 moles) was added slowly at 70° C. to 80° C. The reaction mixture was refluxed using Dean-Stark apparatus to remove approximately 40 mL water. The reaction mixture was cooled to 50° C. to 60° C. and then slowly phosphorous oxychloride (301.18 g, 1.964 moles) was added below 60° C. to 70° C., stirred for 10 min and heated at 100° C. to 110° C. for 3.0 h. The reaction mixture allowed to cool to 25° C. to 30° C. and extracted with water (1800 mL) and aqueous solution was basified with 50% caustic lye solution to pH 5.0 to 5.5. To the reaction mixture a solution of sodium borohydride (33.5 g, 0.886 moles) in water (67.5 mL) and 50% caustic lye solution (0.9 mL) was added in 2 to 3 h and stirred at 25 to 30° C. for 5.0 h. Toluene (900 mL) was added and pH was maintained to 8.5 to 9.0 using 50% caustic lye solution (~165 mL). The aqueous layer was separated from reaction mixture, extracted with toluene (1200 mL) combined with main organic layer, washed with water (1200 mL) and evaporated under reduced pressure to yield dark brown coloured thick solution of Formula (IV) (605.7 g, 99% yield).

EXAMPLE 2.0

(R) and (S)-1-(4-methoxy-benzyl)-1,2,3,4,5,6,7,8-octahydro-isoquinoline-L-mandelate (IVa) and (IVb)

To a stirred solution of 4-methoxyphenyl acetic acid of formula (II), 265.4 g, 1.5970 moles) in 400 mL of xylene, cyclohexenyl ethylamine of formula (III), (200.0 g, 1.5970 moles) was added slowly at 70° C. to 80° C. The reaction mixture was refluxed using Dean-Stark apparatus to remove approximately 23 mL water. The reaction mixture was cooled to 50° C. to 60° C. and then slowly phosphorous oxychloride (200.8 g, 1.3099 moles) was added below 60 to 70° C., stirred for 10 min and heated at 100° C. to 110° C. for 3.0 h. The reaction mixture was allowed to cool to 25° C. to 30° C. and extracted with water (1200 mL) and aqueous solution was washed with toluene (400 mL) and basified with 50% caustic lye solution to pH 5.0 to 5.5. To the reaction mixture a solution of sodium borohydride (31.19 g, 0.8244 moles) in water (61 mL) and 50% caustic lye solution (0.8 mL) was added in 2 to 3 h and stirred at 25° C. to 30° C. for 5.0 h. Toluene (600 mL) was added and pH was maintained to 7.5 to 8.5 using 50% caustic lye solution. The aqueous layer was separated from reaction mixture, extracted with toluene (400 mL) combined with main organic layer and washed with water (800 mL) and brine (400 mL) To above toluene layer, water (680 mL) and S (+)-mandelic acid (158 g, 1.0382 moles) was added and heated to 75° C. to 80° C. for 1.0 h. The reaction mixture allowed to cool gradually to 25° C. to 30° C., filtered, washed with toluene (200 mL) and suck dried. The wet solid compound was dried under vacuum at 50° C. to 55° C. for 6 to 8 h to yield pale yellow coloured solid compound of formula (IVa) & (IVb) (228 g, 34.86% yield) with HPLC purity 59.50% and mandelic acid 40.5%, SOR +133.32°, assay 61.35% and chiral purity of free base 98.63% of formula (IVc, S-isomer) and 1.37% of formula (IVd, R-isomer).

EXAMPLE 3.0

(R) and (S)-1-(4-methoxy-benzyl)-1,2,3,4,5,6,7,8-octahydro-isoquinoline (IVc) and (IVd)

To a solution of racemic compound of formula (IV) (616.0 g, 2.393 moles) in toluene (1017 mL) and water (1017 mL), S (+)-mandelic acid (236.7 g, 1.555 moles) was added and heated to 75° C. to 80° C. for 1.0 h. The reaction mixture was allowed to cool to 25° C. to 30° C., filtered, washed with toluene (800 mL) and suck dried. To the wet cake, water (1200 mL) and toluene (925 mL) was added, pH was maintained to 12.0 to 13.5 using 50% caustic lye solution. The organic layer was separated and evaporated under reduced pressure to yield light yellow coloured solution (204.0 g, 33% yield) with HPLC purity 98%, SOR +146°, chiral purity 98.72% of formula (IVc, S-isomer) and 1.28% of formula (IVd, R-isomer).

EXAMPLE 3.1

(R) and (S)-1-(4-methoxy-benzyl)-1,2,3,4,5,6,7,8-octahydro-isoquinoline (IVc) and (IVd)

To a stirred solution of 4-methoxyphenyl acetic acid of formula (II), (398.2 g, 2.396 moles) in 600 mL of xylene, cyclohexenyl ethylamine of formula (III) (300.0 g, 2.395 moles) was slowly added at 70° C. to 80° C. The reaction mixture was refluxed using Dean-Stark apparatus to remove approximately 40 mL water. The reaction mixture was cooled to 50° C. to 60° C. and then slowly phosphorous oxychloride (301.18 g, 1.964 moles) was added below 60° C. to 70° C., stirred for 10 min and heated at 100° C. to 110° C. for 3.0 h. The reaction mixture was allowed to cool to 25° C. to 35° C. and extracted with water (1.8L) and aqueous solution was basified with 50% caustic lye solution to pH 5.0 to 5.5. To the reaction mixture a solution of sodium borohydride (33.5 g, 0.886 moles) in water (67.5 mL) and 50% caustic lye solution (0.9 mL) was added in 2 to 3 h and stirred at 25° C. to 30° C. for 5.0 h. Toluene (900 mL) was added and pH was maintained to 8.5 to 9.0 using 50% caustic lye solution (~165 mL). The aqueous layer was separated from reaction mixture, extracted with toluene (1200 mL), combined with main organic layer and washed with water (1200 mL). To the separated organic layer, water (1020 mL), S (+) Mandelic acid was added and heated to 75° C. to 80° C. for 1.0 h. The reaction mixture was allowed to cool to 25° C. to 30° C., filtered, washed with toluene (800 mL) and suck dried. To the wet cake water (1200 mL) and toluene (925 mL) was added and the pH was maintained to 12.0 to 13.5 using 50% caustic lye solution. The organic layer was separated and evaporated under reduced pressure to yield light yellow coloured solution (204.0 g, 33% yield) with HPLC purity 98%, SOR +146°, chiral purity 98.72% of formula (IVc, S-isomer) and 1.28% of formula (IVd, R-isomer).

EXAMPLE 4.0

(S)-1-(4-methoxy-benzyl)-3,4,5,6,7,8-hexahydro-1H-isoquinoline-2-carboxylic acid tert-butyl ester (V)

To a stirred solution of (5)-1-(4-methoxy-benzyl)-1,2,3,4,5,6,7,8-octahydro-isoquinoline of formula (IVc, 190 g, 0.738 moles) in dichloromethane (760 mL) and triethylamine (111.8 g, 1.104 moles) was added, cooled to 0° C. to 5° C. To this reaction mixture a solution of di-tert-butyl dicarbonate (177.2 g, 0.812 moles) in dichloromethane (190 mL) was added slowly at 0° C. to 5° C. and stirred at 25° C. to 30° C. for 2.0 h. The clear reaction mixture was washed with 1N HCl solution, saturated sodium bicarbonate solution and organic layer was evaporated under reduced pressure to yield a semisolid compound of formula (V) (253.3 g to 261.2 g, 96 to 99% yield)

LCMS: 358 [M+H]$^+$, HPLC purity: 97 to 99%
$^1$H-NMR: (CDCl3, 400 MHz) 7.01-7.07 (m, 2H), 6.79-6.81 (d, J=8.4 Hz, 2H), 4.08-4.20 (m, 1H), 3.76 (s, 3H), 2.78-3.00 (m, 2H), 2.62-2.73 (m, 1H), 2.14-2.18 (m, 2H), 1.84-1.91 (m, 3H), 1.63-1.69 (m, 6H), 1.34 (m, 3H), 1.17 (s, 6H).

EXAMPLE 5.0 cis:trans (S)-2-(4-methoxy-benzyl)-11-oxa-3-aza-tricyclo[4.4.1.0*1,6*]undecane-3-carboxylic acid tert-butyl ester (VIa and VIb)

To a stirred solution of (S)-1-(4-methoxy-benzyl)-3,4,5,6,7,8-hexahydro-1H-isoquinoline-2-carboxylic acid tert-butyl ester (V, 150.0 g, 0.419 moles) in dichloromethane (1200 mL)

meta-chloroperoxybenzoic acid (119.1 g, 0.690 moles) was added lot wise at 0° C. to 5° C. for 1.0 h. The reaction mixture was allowed to warm to 25° C. to 30° C. and stirred for 2.0 h. The resulting solid was filtered and filtrate was washed with 1M sodium bisulfite, saturated sodium bicarbonate till effervescences stopped. The organic layer further was washed with water, brine and evaporated under reduced pressure to yield light brown colour semisolid compound (150.0 g, 95.7% yield). These compounds are separated by chromatographic technique using hexane-ethyl acetate mobile phase for isolation and characterisation of novel intermediates cis(S)-2-(4-methoxy-benzyl)-11-oxa-3-aza-tricyclo[4.4.1.0*1,6*]undecane-3-carboxylic acid tert-butyl ester (VIa, cis-isomer).

$^1$H-NMR: (CDCl3, 400 MHz) 7.12-7.14 (d, J=8.4 Hz, 1H), 7.03-7.05 (d, J=8.4 Hz, 1H), 6.73-6.77 (m, 2H), 4.14-4.43 (m, 1H), 3.61-3.88 (m, 1H), 3.71 (s, 3H), 2.68-2.90 (m, 3H), 1.34-1.82 (m, 8H), 1.30 (s, 4H), 1.18 (s, 7H)

LCMS: 374 [M+H]$^+$, HPLC purity: 71% trans(S)-2-(4-methoxy-benzyl)-11-oxa-3-aza-tricyclo [4.4.1.0*1,6*]undecane-3-carboxylic acid tert-butyl ester (VIb, trans-isomer)

$^1$H-NMR: (DMSO-d6, 400 MHz) 7.06-7.08 (d, J=8.4 Hz, 2H), 6.82-6.85 (m, 2H), 4.23-4.37 (m, 1H), 3.70 (s, 3H), 3.16-3.40 (m, 1H), 2.94-3.05 (m, 2H), 2.72-2.80 (m, 1H), 1.98-2.04 (m, 1H), 1.39-1.83 (m,6H), 1.30 (s, 7H), 1.16(s, 5H)

LCMS: 374 [M+H]$^+$, HPLC purity: 26%.

EXAMPLE 6.0 cis:trans (S)-1-(4-methoxy-benzyl)-octahydro-iso-quinoline-4a,8a-diol (VIIa and VIIb)

The reaction mixture containing solution of cis:trans (S)-2-(4-methoxy-benzyl)-11-oxa-3-aza-tricyclo [4.4.1.0*1, 6*]undecane-3-carboxylic acid tert-butyl ester (VIa and VIb, 155.0 g, 0.415 moles) in acetone (465 mL) was cooled to 0° C. to 5° C. and water (132.66 mL) was added. To the reaction mixture concentrated sulphuric acid (244.09 g, 2.489 moles) was added dropwise below 0 to 15° C. and heated at 40° C. to 45° C. for 3.0 h. The reaction mixture was cooled to 0° C. to 5° C., water (1550 mL) was charged and pH was adjusted to 12.0 to 12.5 using 50% caustic lye solution (~115 mL) below 20° C. The reaction mixture was allowed to warm to 40° C. to 45° C., stirred for 1.0 h, filtered, washed with water (775 mL) and dried to yield (95.0 g, 78.9% yield) as an off-white solid with HPLC purity 78.11% (VIIb, trans-isomer) and 19.89% (VIIa, cis- isomer).

EXAMPLE 6.1 cis:trans (S)-1-(4-methoxy-benzyl)-octahydro-iso-quinoline-4a,8a-diol (VIIa and VIIb)

To a stirred solution of (S)-1-(4-methoxy-benzyl)-1,2,3,4,5,6,7,8-octahydro-isoquinoline-L-Mandelate of formula (IVa,210 g, 0.5128 moles) in mixture of dichloromethane (840 mL), water (840 mL) was added and basified with 50% caustic lye solution (~105 g, 1.3125 moles) to pH >12. The aqueous layers are separated, extracted with dichloromethane (420 mL) and combined organic layer was washed with water (630 mL), brine (420 mL) solution. To the separated organic layer triethyl amine (77.8 g. 0.7691 mole) was added and cooled to 0° C. to 5° C. To the reaction mixture a solution of di-tert-butyl dicarbonate (123.13 g, 0.5641 moles) in dichloromethane (210 mL) was added slowly at 0° C. to 5° C. and stirred at 25° C. to 30° C. for 2.0 h. The reaction mixture was quenched with water (630 mL), organic layer separated and acidified with 1N HCl solution under stirring till the pH of aqueous solution becomes 4.0 to 5.0. The organic layer separated, washed with brine (420 mL) and the separated organic layer was cooled to 0° C. to 5° C. To the cooled reaction mixture, the meta-chloroperoxybenzoic acid (140.11 g, 0.6150 moles) was added lot wise at 0° C. to 5° C. and allowed to warm to 25° C. to 30° C. and further stirred for 2.0 h. The solid was filtered and filtrate was washed with 1M sodium bisulfite solution (630 mL×3), with 5% sodium bicarbonate solution (630 mL×3), water (630 mL) and with brine solution (420 mL). The organic layer was separated and evaporated under reduced pressure to yield light brown colour semisolid compound. To this semisolid compound acetone (567 mL) was added, cooled to 0° C. to 5° C. and water (163 mL) was added. To the reaction mixture, concentrated sulphuric acid (163.8 mL, 3.0830 moles) was added drop wise below 15° C., warmed to 40° C. to 45° C. and stirred for 3 h. The reaction mixture was cooled to 0° C. to 5° C. and water (2100 mL) was added at 0° C. to 5° C. The pH was adjusted to 12 to 13 using 50% caustic lye solution. The reaction mixture was filtered and washed with water (1050 mL). To the wet cake water (2100 mL) was added and heated at 40° C. to 45° C. for 1 h. The reaction mixture was filtered at 40° C. to 45° C., washed with water (1050 mL) and dried under vacuum at 50° C. to 55° C. to yield light brown to pale yellow solid of formula (VIIa, VIIb) (114.5 g, 76.6% yield) with HPLC purity 74.34% (S-isomer), 24.20% (R-isomer). Assay=96.51%, sulphated ash=0.08%.

EXAMPLE 7.0 cis:trans (S)-2-cyclobutylmethyl-1-(4-methoxy-benzyl)-octahydro-isoquinoline-4a,8a-diol (VIIIa and VIIIb)

To the solution of cis:trans (S)-1-(4-methoxy-benzyl)-octahydro-isoquinoline-4a,8a-diol of formula (VIIa and VIIb, 25.0 g, 0.0857 moles) in DMF (100 mL), sodium bicarbonate (18.0 g, 0.214 moles), cyclobutylmethyl bromide (16.2 g, 0.112 mole) was added at 25° C. to 30° C. The reaction mixture was heated at 100° C. and stirred for 10 h. After completion, the reaction mixture was cooled to 25° C. to 30° C. and water (250 mL) was added dropwise for 30 min. Reaction mixture was filtered, washed with water (125 mL) and dried to (26.0 g) yield crude compound. The crude compound was purified by stiffing with IPA (50 mL) at 5° C. to 10° C. for 1.0 h. After 1.0 h reaction mixture was filtered, washed with cold IPA (25 mL) and dried to yield (22.6 g, 73% yield) as a off white solid with HPLC purity 89.86% of formula (VIIIb, trans-isomer) and 9.29% of formula (VIIIa, cis-isomer).

EXAMPLE 7.1 cis:trans ((S)-2-cyclobutylmethyl-1-(4-methoxy-benzyl)-octahydro-isoquinoline-4a,8a-diol (VIIIa and VIIIb)

To the stirred solution of cis:trans mixture of(S)-1-(4-methoxy-benzyl)-octahydro-isoquinoline-4a,8a-diol of formula (VIIa and VIIb, 570 g, 1.956 moles) in DMF (2.28 Lit) sodium bicarbonate (410 g, 4.890 moles) and cyclobutylmethyl bromide (378.9 g, 2.543 mole) was added at 25° C. to 30° C. The reaction mixture was heated at 100° C. to 110° C. and stirred for 10 h. The reaction mixture was cooled to 25° C. to 30° C., water (5.7 Lit) was added drop wise below 40° C. and solid was filtered, washed with water (2.8 Lit). To the crude wet solid compound water (5.7 Lit) was added and heat to 40° C. to 45° C., further stirred for 1.0 h. The solid was filtered at 40° C. to 45° C. and washed with water (2.8 Lit) and dried under vacuum at 50° C. to 55° C. for 8.0 h. To the crude compound IPA (1.710 Lit) was added and further heated to reflux for 1.0 h to clear solution. The reaction mixture was allowed to cool to 10° C. to 15° C., filtered, washed with cold IPA (570 mL) and dried under vacuum at 50° C. to 55° C. for 5.0 h to yield light brown to pale yellow solid compound (491g, 69.8% yield) of formula (VIIIa, VIIIb) with HPLC purity 84.49% (S-isomer) and 15.48% (R-isomer) assay 99.55%, moisture content 0.09%, sulphated ash=0.30%.

EXAMPLE 8.0

N-cyclobutylmethyl-14-hydroxy-3-methoxymorphinan (IX)

To a cis:trans (S)-2-cyclobutylmethyl-1-(4-methoxy-benzyl)-octahydro-isoquinoline-4a,8a-diol (VIIIa and VIIIb, 5.0 g, 0.014 moles) 1M Borane-THF solution (16.8 mL) was added slowly at 25° C. to 30° C. and stirred for 30 min. The solvent from reaction mixture was evaporated at 50° C. under reduced pressure to yield light brown residue. To this residue anhydrous polyphosphoric acid (75.0 g, 0.765 moles) was added at 40° C. to 45° C. for 6.0 h. The reaction mixture was cooled to 5° C. to 10° C. and water (75 mL) was added dropwise and adjusted to pH 8.0 to 9.0 using liquid ammonia (115 mL). The reaction mixture was extracted with ethyl acetate (50 mL×3) and combined organic layer washed with water (75 mL) and brine (10 mL) solution. The organic layer evaporated under reduced pressure to yield (3.66 g, 77% yield) as light brown oily compound of formula (IX) with HPLC purity 71.14%.

EXAMPLE 9.0

N-cyclobutylmethyl-3,14-dihydroxymorphinan (X)

To an ice cooled solution of N-cyclobutylmethyl-14-hydroxy-3-methoxymorphinan of formula (IX, 4.5 g, 0.0132 moles) in dichloromethane (45.0 mL) 1M $BBr_3$ solution in dichloromethane (26.4 mL) was added dropwise at 0° C. to 5° C. and stirred for 30 min. The reaction mixture was allowed to warm to 25° C. to 30° C. and stirred for 3.0 h. The reaction mixture was further cooled to 0° C. to 5° C., water (22.5 mL) was added and pH was adjusted to 8.0 to 9.0 using liquid ammonia (9.0 mL) The reaction mixture was extracted with dichloromethane (45.0 mL×2) and combined organic layer washed with water (45.0 mL) and brine solution (9.0 mL). The organic layer was evaporated under reduced pressure to yield (4.67 g) crude compound as a light brown solid. The crude compound was stirred in methanol (9.0 mL) at 0° C. to 5° C., filtered and dried to yield (2.51 g, 59% yield) as an off-white solid of formula (X) with HPLC purity 98.38%.

EXAMPLE 9.1

N-cyclobutylmethyl-3,14-dihydroxymorphinan (X)

To cis: trans (S)-2-cyclobutylmethyl-1-(4-methoxy-benzyl)-octahydro-isoquinoline-4a,8a-diol (VIIIa and VIIIb, 450 g, 1.2500 moles) 1M Borane-THF solution (1.377 L) was added slowly at 25° C. to 30° C. and stirred for 30 min. The solvent from reaction mixture was evaporated at 50° C. under reduced pressure to yield light brown residue. To this residue anhydrous phosphoric acid (4.5 Kg, 45.92 moles) was added at 40° C. to 45° C. and stirred for 16.0 h. The reaction mixture was cooled to 10° C. to 15° C. and water (4.5 L) was added drop wise. To the reaction mixture dichloromethane (4.5 L) was added and pH was adjusted to 7.0 to 8.0 using 25% liquid ammonia (6.9 L). The reaction mixture was extracted with dichloromethane (2.250 L) and combined organic layer washed with water (4.5 L), brine (1.35 L) solution. The organic layer was cooled to 0° C. to 5° C. and 1M BBr$_3$ solution in dichloromethane (2.5 Lit) was added drop wise at 0° C. to 5° C. The reaction mixture allowed to warm to 25° C. to 30° C., stirred for 3.0 h and further cooled to 0° C. to 5° C. and water (4.5 L) was added and pH was adjusted to 8.0 to 9.0 using liquid ammonia (450 mL) The organic layer was separated and aqueous layer was extracted with dichloromethane (2.25 L), combined organic layer washed with water (4.5 L×2) and evaporated under reduced pressure to yield brown coloured crude compound. The crude compound was stirred in methanol (900 mL) at 25° C. to 35° C., treated with activated carbon in acetone (5.6 L), filtered, washed with dichloromethane (280 mL) and further dried at 50° C. to 55° C. to yield off white to white powder (125 g, 30.5% yield) of formula (X) with HPLC purity 99.87%, chiral purity 100%, assay 99.48%, sulphated ash 0.09%, moisture content 0.15%.

EXAMPLE 10.0

Morphinan-3,14-diol1,17-(cyclobutylmethyl )-,(−)-, [S-(R*,R*)]-2,3-dihydroxybutanedioate salt (I)

The reaction mixture containing (−)-17-(Cyclobutylmethyl)-3,14b-dihydroxy morphinan (X), 100 g, 0.305 moles) in methanol (400 mL) was heated at 65° C. To the reaction mixture, solution of D(−) tartaric acid (45.83 g, 0.305 moles) in hot methanol (200 mL) was added and stirred at 65° C. for 30 min. The reaction mixture was cooled to 40° C. to 45° C., acetone (800 mL) was added, allowed to cool to 25° C. to 30° C., stiffed, filtered the solid and further dried at 50° C. to 55° C. to yield a white powder (127 g, 87.08% yield) of formula (I) with HPLC purity 97.22% (free base), tartaric acid purity 2.73%, chiral purity 99.96% (S-isomer), 0.04% (R-isomer) and SOR: −64.76°.

EXAMPLE 11.0

(R) 1-(4-Methoxy-benzyl)-1,2,3,4,5,6,7,8-octahydro-isoquinoline (IVd)

The main filtrate and toluene washing of example-2 of formula (IVa) was combined, pH was adjusted to 12 to 13.5 using 50% caustic lye solution (227 g, 2.840 moles) at 25° C. to 30° C. and stirred for 30 min. The organic layer was separated and aqueous layer was extracted with toluene (250 mL×2) and combined organic layer was washed with water (250 mL) dried over sodium sulphate and evaporated under reduced pressure at 45° C. to 50° C. to yield dark brown thick oily mass of R-isomer (233 g, 58.25% yield) of formula (IVd) with HPLC purity 90.86%, SOR: −92.63°.

EXAMPLE 12.0

1-(4-Methoxy-benzyl)-1,2,3,4,5,6,7,8-octahydro-isoquinoline (IV)

To a stirred and cooled solution of (R)-1-(4-methoxy-benzyl)-1,2,3,4,5,6,7,8-octahydro-isoquinoline (IVd, 100 g, 0.3885 moles) in MTBE (500 mL), 9% sodium hypochloride solution (256 mL) was slowly added at −5° C. to −10° C. The reaction mixture was warmed to 5° C. to 10° C., stirred for 2 h, further warmed to 20° C. to 25° C. and stirred for 2 h. The organic layer was separated, aqueous layer extracted with methyl tert-butyl ether (400 mL) and combined organic layer dried over sodium sulphate and cooled to 5° C. to 10° C. and a solution of potassium hydroxide (116.84 g, 2.0820 moles) in methanol (300 mL) was added slowly. The reaction mixture was warmed to 20° C. to 25° C. and stirred for 2 h and water (300 mL) was added and further cooled to 5° C. to 10° C. The solution of sodium borohydride (25.86 g, 0.6830 moles) and NaOH (8 g, 0.1990 moles) in water (200 mL) was added slowly and reaction mixture was warmed to 20° C. to 25° C. and stirred for 2 h. The organic layer separated and aqueous layer was extracted with methyl tert-butyl ether (400 mL), combined organic layer was washed with water (400 mL) and evaporated under reduced pressure to yield brown thick gummy mass (83 g, 83% yield) of racemic compound of formula (IV) with chiral purity: 50.43% S-isomer, and 49.57%, R-isomer.

SUBSTANTIAL ADVANTAGES AND INDUSTRIAL APPLICABILITY (1) The process of the present invention is safe and yields higher chemical purity and greater yield of a compound of formula (I) and many of the steps are performed in in-situ manner (2) The process of the present invention avoids excess usages of reagent(s) and organic solvent(s), thereby promoting green chemistry and ensuring a cleaner surrounding by putting lesser load on environment.

(3) The process of the present invention avoids the use of solvents like benzene, which are harmful for the environment and is very hazardous in nature.

(4) The process of the present invention uses a solvent and intermediate(s) which can be recycled and reused and thus makes the process more economical and industrially & commercially viable.

(5) The process of the present invention is a simple process, which avoids more number of operations, thus resulting in shortening of reaction time and lowering of labour.

The invention claimed is:

1. An improved process for the preparation of Butorphanol tartrate of formula (I),

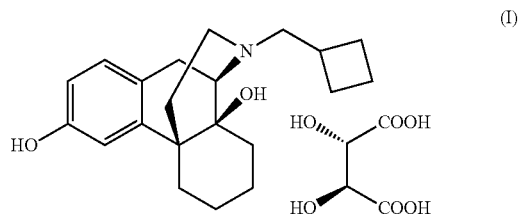

comprising the steps of:
(a) obtaining a compound of formula (IV) by reacting a compound of formula (II) with a compound of formula (III) in suitable conditions;

(II)

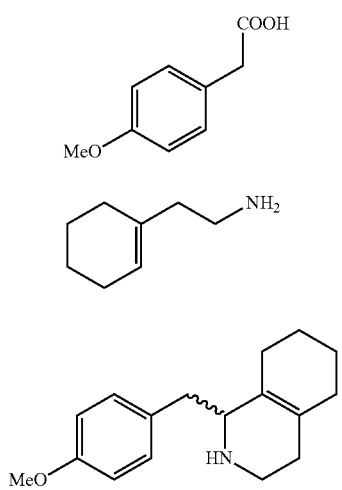

(III)

(IV)

(b) resolving a compound of formula (IV) to obtain a mixture of compound of formula (IVa) and (IVb) using a suitable resolving agent in a suitable solvent to further obtain a mixture of compound of formula (IVc) and (IVd);

(IVa)

(IVb)

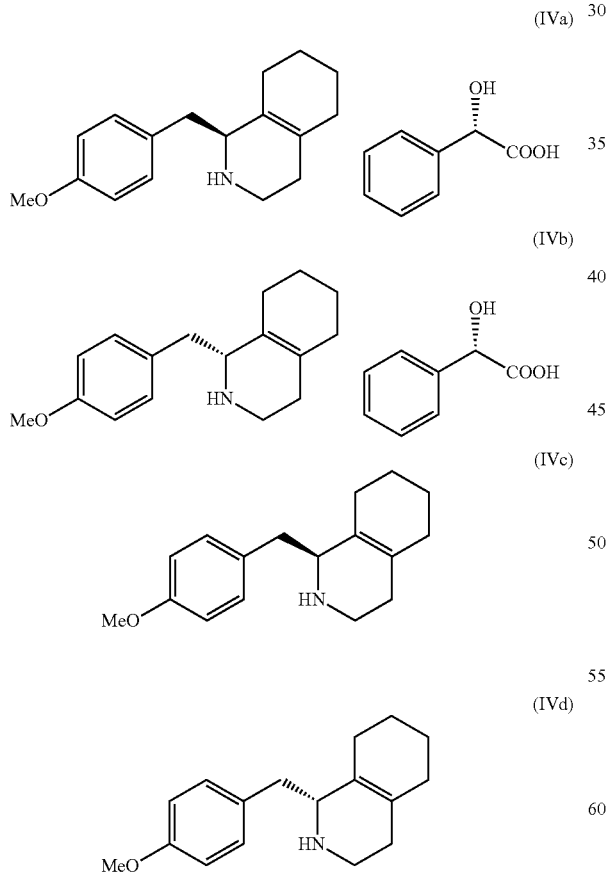

(IVc)

(IVd)

(c) protecting a compound of formula (IVc) with di-tert-butyl dicarbonate in presence of a suitable base in a suitable solvent to get a compound of formula (V);

(V)

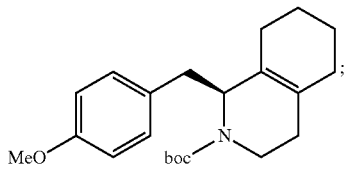

wherein boc is tert-butoxycarbonyl (d) obtaining a mixture of compound of formula (VIa) and (VIb) by the epoxidation of compound of formula (V) with peroxy acid in a suitable solvent;

(VIa)

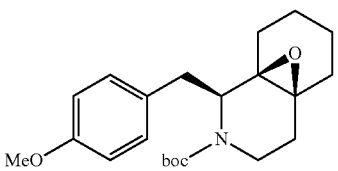

(VIb)

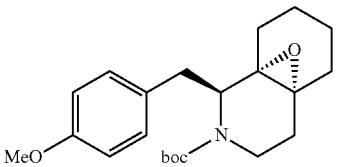

(e) obtaining a mixture of compound of formula (VIIa) and (VIIb) by acid catalyzed ring opening and deprotection of mixture of compounds of formula (VIa) and (VIb) with a suitable acid in a suitable organic solvent;

(VIIa)

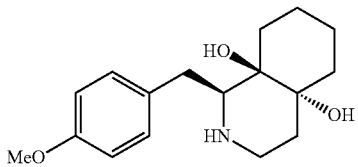

(VIIb)

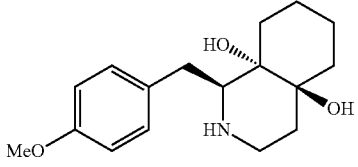

(f) obtaining a mixture of compound of formula (VIIIa) and (VIIIb) by reacting a mixture of compound of formula (VIIa) and (VIIb) with cyclobutylmethyl bromide in presence of a suitable base in a suitable solvent;

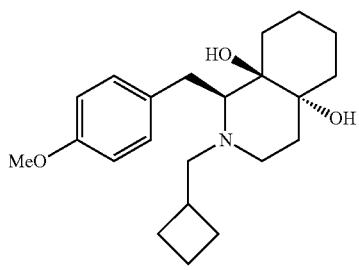

(VIIIa)

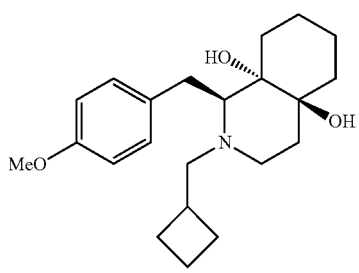

(VIIIb)

(g) cyclizing a mixture of compound of formula (VIIIa) and (VIIIb) with borane in presence of an anhydrous acid with or without suitable organic solvent to obtain a compound of formula(IX);

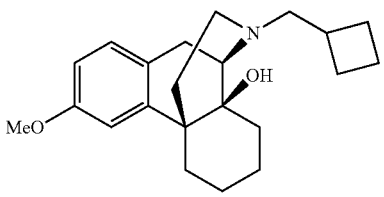

(IX)

(h) demethylating a compound of formula (IX) using a suitable demethylating agent in a suitable solvent to obtain Butorphanol of formula(X); and

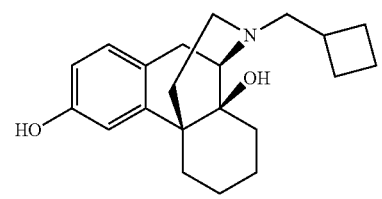

(X)

(i) obtaining Butorphanol tartrate salt of formula (I) from Butorphanol of formula (X) by using tartaric acid in a suitable organic solvent.

2. The process as claimed in claim 1, wherein all the steps or some of the steps are performed in in-situ manner.

3. The process as claimed in claim 1, wherein the said suitable conditions in step (a) comprises condensing of a compound of formula (II) with a compound of formula (III) using an organic solvent under reflux conditions, cyclizing using an acid in organic solvent and further reducing with suitable reducing agent in presence of a suitable base.

4. The process as claimed in claim 1, wherein the said solvent used in step (a) and step (b) is selected from the group consisting of water, xylene, benzene, toluene, ethylbenzene, cyclohexane, and a mixture of solvents thereof.

5. The process as claimed in claim 1, wherein the said acid used in step (a) is phosphorus oxychloride.

6. The process as claimed in claim 3, wherein the said reducing agent used in step (a) is selected from the group consisting of sodium borohydride, lithium borohydride and lithium aluminium hydride.

7. The process as claimed in claim 1, wherein the said base of step (a), step (c) and step (f) is selected from an organic base and an inorganic base.

8. The process as claimed in claim 7, wherein the said an organic base is selected from the group consisting of pyridine, mono, di and tri alkyl amine; and the said an inorganic base is selected from the group consisting of potassium carbonate, sodium carbonate, sodium bicarbonate, potassium bicarbonate, alkali metal hydroxides and alkaline earth metal hydroxides.

9. The process as claimed in claim 7, wherein the base in step (a) is sodium hydroxide, in step (c) is triethyl amine, and in step (f) is sodium bicarbonate.

10. The process as claimed in claim 1, wherein the said resolving agent used in step (b) is S(+) mandelic acid.

11. The process as claimed in claim 1 wherein, the said solvent used in step (c), step (d), step (e) and step (h) is a chlorinated solvent.

12. The process as claimed in claim 1, wherein the said peroxy acid used in step (d) is m-chloroperbenzoic acid.

13. The process as claimed in claim 1, wherein the said acid used in step (e) is sulfuric acid.

14. The process as claimed in claim 1, wherein the said solvent used in step (e) is selected from the group consisting of water, acetone, methyl ethylketone, methyl isobutyl ketone and mixtures.

15. The process as claimed in claim 1, wherein the said solvent used in step (f) is one or more polar aprotic solvent.

16. The process as claimed in claim 1, wherein the said acid used in step (g) is polyphosphoric acid.

17. The process as claimed in claim 1, wherein the said solvent used in step (g) is tetrahydrofuran, which is in the form of borane-tetrahydrofuran complex.

18. The process as claimed in claim 1, wherein the said demethylating agent in step (h) is selected from the group consisting of sodium dithionate, potassium dithionate, barium dithionate, boron tribromide, phosphorus tribromide and mixtures thereof.

19. The process as claimed in claim 1, wherein the said solvent used in step (i) is selected from the group consisting of methanol, ethanol, isopropanol, n-propanol, n-butanol, acetone, methyl ethyl ketone, methyl isobutyl ketone, and mixtures thereof.

20. A compound of formula (V):

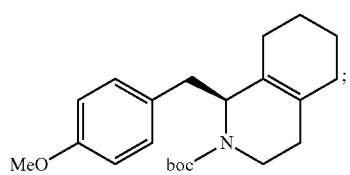

(V)

wherein boc is tert-butoxycarbonyl.

21. A compound of formula (VIa) or (VIb):

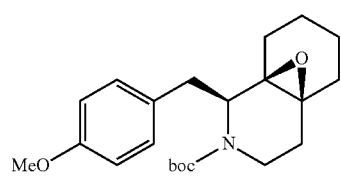
(VIa)

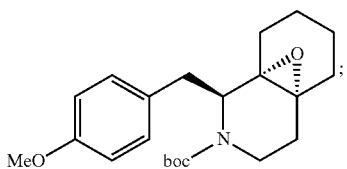
(VIb)

wherein boc is tert-butoxycarbonyl.

22. A method for the preparation of Butorphanol or a salt thereof, the method comprising:
(a) the epoxidation of compound of formula (V):

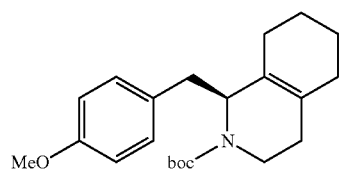
(V)

wherein boc is tent-butoxycarbonyl;
with a peroxy acid in a suitable solvent, to provide a mixture of compounds of formula (VIa) and (VIb):

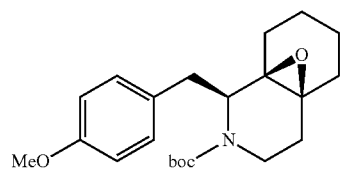
(VIa)

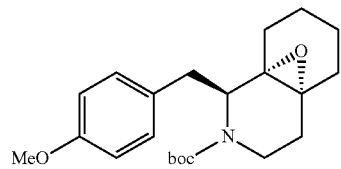
(VIb)

(b) obtaining a mixture of compound of formula (VIIa) and (VIIb) by acid catalyzed ring opening and deprotection of mixture of compounds of formula (VIa) and (VIb) with a suitable acid in a suitable organic solvent;

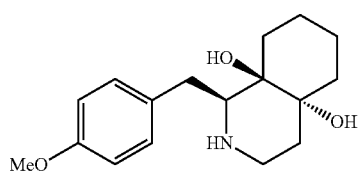
(VIIa)

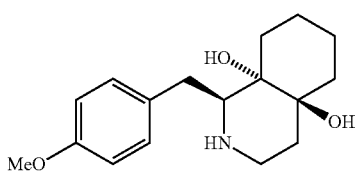
(VIIb)

(c) obtaining a mixture of compound of formula (VIIIa) and (VIIIb) by reacting a mixture of compounds of formula (VIIa) and (VIIb) with cyclobutylmethyl bromide in presence of a suitable base in a suitable solvent;

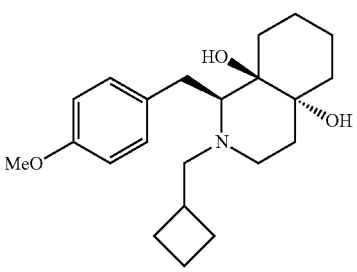
(VIIIa)

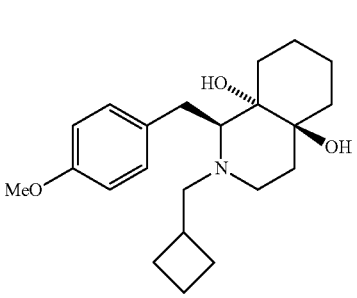
(VIIIb)

(d) cyclizing a mixture of compound of formula (VIIIa) and (VIIIb) with borane in presence of an anhydrous acid with or without suitable organic solvent to obtain a compound of formula (IX);

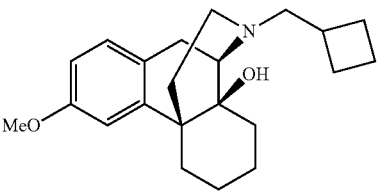
(IX)

(e) demethylating a compound of formula (IX) using a suitable demethylating agent in a suitable solvent to obtain Butorphanol of formula (X);

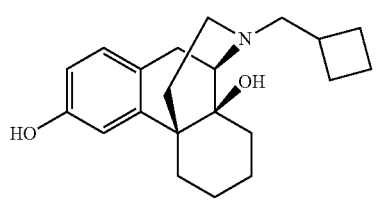 (X)
and
(f) optionally obtaining Butorphanol tartrate salt of formula (I):
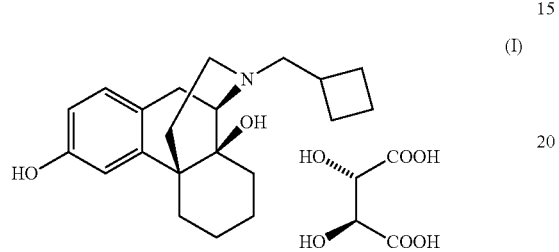 (I)
from Butorphanol of formula (X) by combining Butorphanol of formula (X) with tartaric acid in a suitable organic solvent.
* * * * *

UNITED STATES PATENT AND TRADEMARK OFFICE
CERTIFICATE OF CORRECTION

PATENT NO. : 10,544,101 B2  
APPLICATION NO. : 16/089505  
DATED : January 28, 2020  
INVENTOR(S) : Rahul Bhalerao et al.

Page 1 of 1

It is certified that error appears in the above-identified patent and that said Letters Patent is hereby corrected as shown below:

In the Claims

• In Claim 14, at Column 36, Line 36, please insert -- *thereof.* -- at the end of the claim;

• In Claim 22, at Column 38, Line 11, please delete "*ViIIIa*" and insert -- *VIIIa* -- therefor.

Signed and Sealed this  
Twenty-eighth Day of April, 2020

Andrei Iancu  
*Director of the United States Patent and Trademark Office*